United States Patent [19]

Ohkubo et al.

[11] Patent Number: 5,403,938
[45] Date of Patent: Apr. 4, 1995

[54] POLYTHIOL COMPOUND, AND OPTICAL MATERIAL AND PRODUCT PRODUCED THEREFROM

[75] Inventors: Tsuyoshi Ohkubo, Hachioji; Chau Nguyen, Ohme; Reisuke Okada, Hinodemachi, both of Japan

[73] Assignee: Hoya Corporation, Tokyo, Japan

[21] Appl. No.: 73,663

[22] Filed: Jun. 8, 1993

Related U.S. Application Data

[62] Division of Ser. No. 633,304, Dec. 24, 1990.

[30] Foreign Application Priority Data

Dec. 28, 1989 [JP] Japan .................................. 1-343298
Oct. 19, 1990 [JP] Japan .................................. 2-281089

[51] Int. Cl.⁶ ........................................... C07D 339/00
[52] U.S. Cl. ..................................... 549/22; 252/582
[58] Field of Search ................... 252/582, 587, 589; 528/85, 377; 549/14, 22

[56] References Cited

U.S. PATENT DOCUMENTS

| 2,891,072 | 6/1959 | Remes | 528/377 |
| 2,900,392 | 8/1959 | Remes | 528/377 |
| 4,225,700 | 9/1980 | Wolfe et al. | 528/377 |
| 5,084,545 | 1/1992 | Nagata et al. | 528/85 |

FOREIGN PATENT DOCUMENTS

351073 1/1990 European Pat. Off. .
823352 11/1959 United Kingdom .

*Primary Examiner*—Philip Tucker
*Attorney, Agent, or Firm*—Nixon & Vanderhye

[57] ABSTRACT

This invention relates-to a polythiol compound and an optical material therefrom. Having a rigid 1,4-dithian ring which increases the refractive index and Abbe's number, the polythiol compound used for the production of an optical material imparts the optical material with high heat resistance and excellent mechanical properties as well as excellent optical properties.

4 Claims, 2 Drawing Sheets

POLYTHIOL COMPOUND, AND OPTICAL MATERIAL AND PRODUCT PRODUCED THEREFROM

This is a division of application Ser. No. 07/633,304, filed Dec. 24, 1990, now allowed.

BACKGROUND OF THE INVENTION

1. Field of the Invention

This invention relates to a polythiol compound, and an optical material and optical product comprising same. The polythiol compound of this invention is used, e.g. as a useful material for an optical material. The optical material produced from the above polythiol compound, provided by this invention, exhibits a high refractive index and low dispersion or has excellent optical properties, and it is preferred for use in optical products such as a plastic lens, a prism, an optical fiber, a substrate for data reading and storage, a colored filter, an infrared absorbing filter, etc.

Further, it is usable in ornament such as a cup, a flower vase. etc., owing to a high refractive index which the material has as a characteristic.

2. Description of Prior Art

Being light-weighted, unbreakable to a certain degree and easy to dye as compared with glass, plastic has been recently used for an optical purpose, e.g. for producing various lenses. For this reason, polyethylene glycol bisallylcarbonate (CR-39) and polymethyl methacrylate (PMMA) are generally used as a plastic material. Since, however, these plastic materials have a refractive index of not more than 1.50, a lens formed of such a plastic material is required to have a large thickness when the degree is increased. As a result, undesirably, not only the advantage of the light-weight of plastic is lost, but also aesthetic appearance of spectacles of such a material is poor. In particular, when a concave lens is formed of such a material, the peripheral thickness of the lens increases, and birefringence and chromatism undesirably take place. It is therefore desired to develop a plastic material which can take advantage of the properties of plastic having low specific gravity or permit a smaller thickness of a lens, and which has low chromatism, a high refractive index and low dispersion. As a material for such purposes, JP-A-63-46213 discloses a polymer of tetrachloro-m-xhylylenedithiol or 1,3,5-trimercaptobenzene with a diisocyanate compound. JP-A-64-26622 discloses a polymer of pentaerythritol-tetrakisthiopropionate with a diisocyanate compound. Further, JP-A-63-309509 discloses a polymer of pentaerythritoltetrakisthiopropionate with a vinyl compound.

However, the thiol compound disclosed in the above JP-A-63-46213 has a low Abbe's number although it has a high refractive index, and a polymer produced therefrom also has defects in that it has a low Abbe's number and poor weatherability. And, the thiol compounds disclosed in JP-A-64-26622 and JP-A-63-309509 have a low refractive index although they have a large Abbe's number, and polymers produced therefrom have defects in that they have a low refractive index and inferior heat resistance.

SUMMARY OF THE INVENTION

It is therefore an object of this invention to provide a novel thiol compound which can overcome the above defects, and novel optical material and product produced from it as a starting material.

This invention has been made to achieve the above object, and the novel thiol compound of this invention has the formula [1].

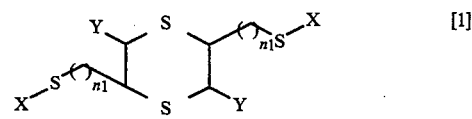

wherein X is $-(CH_2CH_2S)_{n_2}-H$, Y is a hydrogen atom or $-(CH_2)_{n_3}-S-X$, $n_1$ is an integer of 1 to 5, $n_2$ is an integer of 0 to 2, and $n_3$ is an integer of 1 to 5.

The novel optical material of this invention comprises a polymer obtained by polymerizing a component (A) which at least contains a polythiol compound ($a_1$) and a component (B) which contains at least one member of a compound ($b_1$) having at least two vinyl groups per molecule, a compound ($b_2$) having at least two iso(thio)cyanate groups per molecule and a compound ($b_3$) having at least one vinyl group and at least one iso(thio)cyanate group per molecule. In addition, the above "iso(thio)cyanate group" means both an isocyanate group and a thiocyanate group.

DETAILED DESCRIPTION OF THE INVENTION

Figure 1:
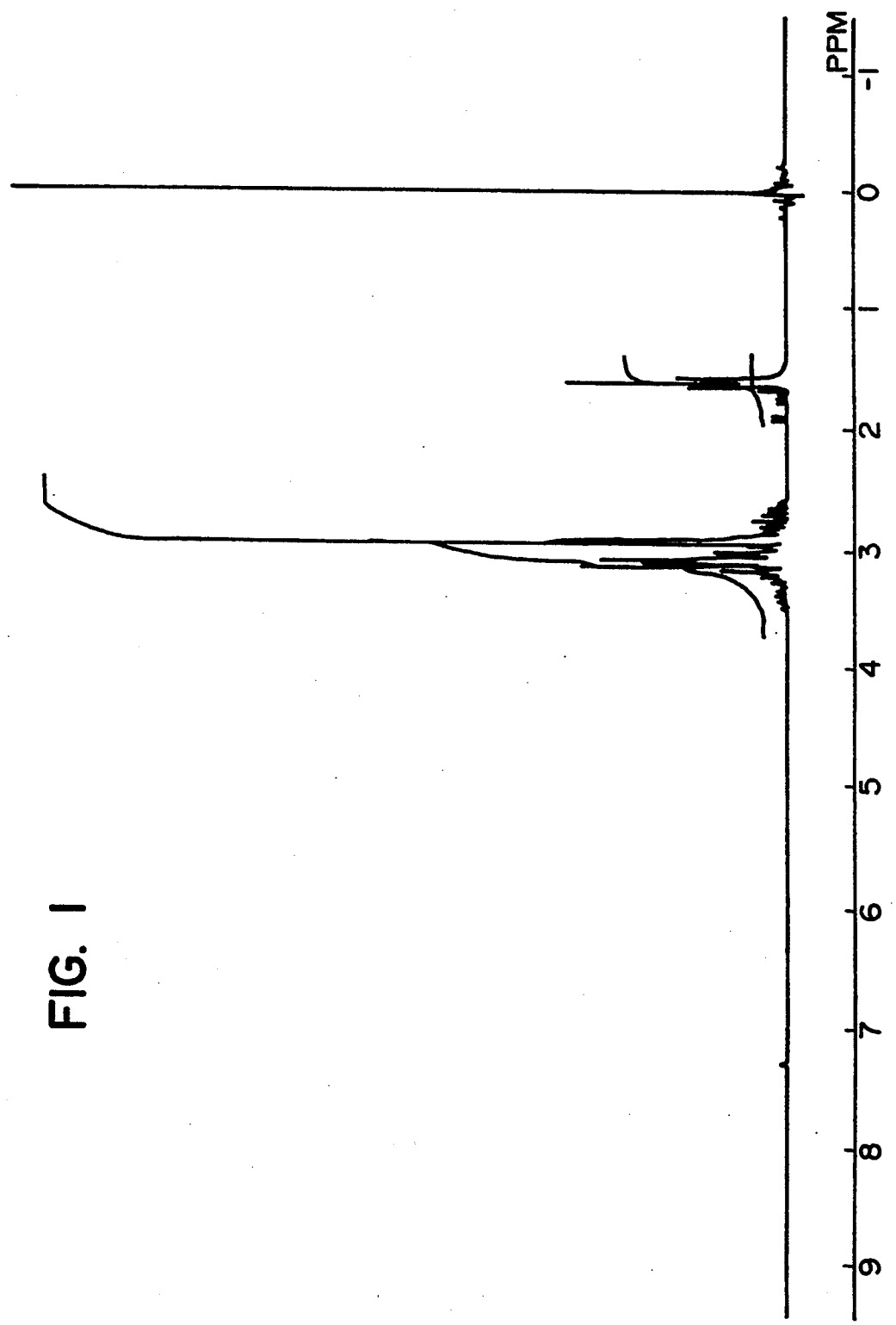
FIGS. 1 and 2 are a $^1$H-NMR spectrum chart and an IR spectrum chart of the polythiol compound obtained in Example 1, respectively.

This invention will be detailed hereinafter.

The novel polythiol compound of this invention has a characteristic feature in that it has a 1,4-dithian ring which is a cyclic sulfide, as is shown in the above formula [1]. The 1,4-dithian ring increases the refractive index and Abbe's number of a polythiol compound. Therefore, this polythiol compound used for the production of a polymer increases the refractive index and Abbe's number of the polymer. The 1,4-dithian ring in a polythiol compound is rigid. Therefore, the polythiol compound used for the production of a polymer impart the polymer with high heat resistance and excellent mechanical properties.

In the formula [1], $n_1$ and $n_3$ are limited to an integer of 1 to 5, and $n_2$ is limited to an integer of 0 to 2. The reasons therefor are as follows. When $n_1$ abd $n_3$ are 0, a polymer produced from the polythiol compound is fragile and its impact resistance is degraded. On the other hand, when $n_1$ and $n_3$ exceed 6, the polythiol compound has a reduced refractive index, and undesirably, a polymer produced therefrom is libale to have not only a reduced refractive index but also degraded heat resistance. Further, when $n_2$ is not less than 3, a polymer produced from the polythiol compound undesirably has degraded heat resistance.

The polythiol compound of this invention can be synthesized according to a method shown in the following scheme, e.g. when it is a compound of the formula [1] in which X is a hydrogen atom ($n_2=0$), Y is a hydrogen atom and $n_1=1$.

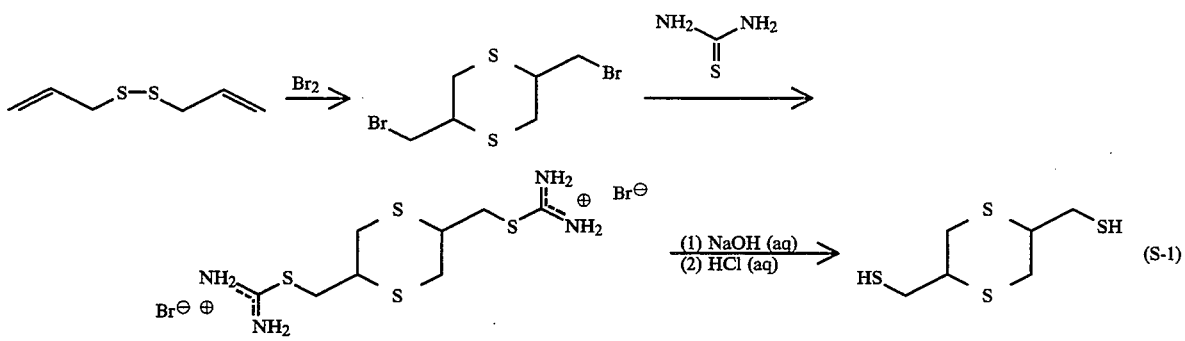

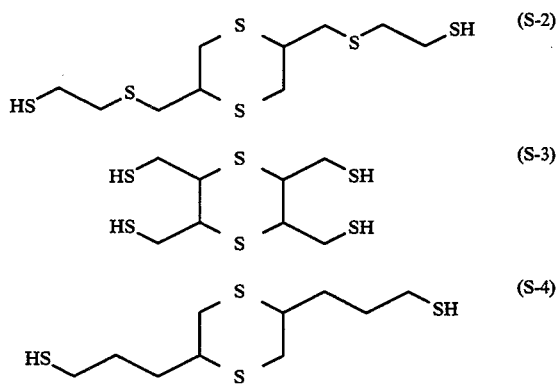

That is, a diallyldisulfide is reacted with bromine, and, a resulting cyclic dimerized compound with bromine atoms is reacted with a thiourea to form an isothiuronium salt. This salt is hydrolyzed with an aqueous sodium hydroxide solution and then acidified with hydrochloric acid, whereby the intended polythiol compound can be obtained.

The following are examples of the polythiol compound of the formula [1] other than the polythiol compound of which the production process is described above and in which X is a hydrogen atom ($n_2=0$), Y is a hydrogen atom and $n_1=1$.

The optical material comprising the polythiol compound of the above formula [1], provided by this invention, is explained below. This optical material comprises a polymer obtained by polymerizing a component (A) which at least contains a polythiol compound ($a_1$) and a component (B) which contains at least one member of a compound ($b_1$) having at least two vinyl groups per molecule, a compound ($b_2$) having at least two iso(thio)cyanate groups per molecule and a compound ($b_3$) having at least one vinyl group and at least one iso(thio)cyanate group per molecule. Since the compound ($a_1$) of the formula [1], contained in the component (A), is detailed above, an explanation thereof is omitted here.

In order to improve physical properties, etc., of the polymer as required, the component (A) may contain one or more compounds ($a_2$) having mercapto group(s) and/or hydroxy group(s) in such a manner that the total number of the mercapto and hydroxy groups per molecule is not less than 2, in addition to the compound ($a_1$) of the formula [1]. Specific examples of the compound ($a_2$) are trimethylolpropane, 1,2-ethanedithiol, 1,3-propanedithiol, tetrakismercaptomethylmethane, pentaerythritoltetrakismercaptopropionate, pentaerythritoltetrakismercaptoacetate, 2-mercaptoethanol, 2,3-dimercaptopropanol, 1,2-dihydroxy-3-mercaptopropane, 4-mercaptophenol, 1,2-benzenedithiol, 1,3-benzenedithiol, 1,4-benzenedithiol 1,3,5-benzenetrithiol, 1,2-dimercaptomethylbenzene, 1,3-dimercaptomethylbenzene, 1,4-dimercaptomethylbenzene, 1,3,5-trimercaptomethlbenzene, toluene-3,4-dithiol and 4,4'-dihydroxyphenylsulfide.

The amount of the compound ($a_1$) of the formula [1] based on the total amount of the component (A) is 0.1 to 100 mol %, preferably 10 to 100 mol %.

Specific examples of the compound ($b_1$) containing vinyl groups, contained in the component (B), are divinylbenzene, ethyleneglycoldi(meth)acrylate, trimethylolpropane- tri(meth)acrylate, urethane-modified (meth)acrylates, epoxy-modified (meth)acrylates and polyester-modified (meth)acrylates. These modified acrylates contain at least two (meth)acryloxy groups per molecule. (In addition, the above "(meth)acrylate" stands for both of an acrylate and a methacrylate, and the "(meth)acryloxy group stands for both of an acryloxy group and a methacryloxy group.)

Specific examples of the compound ($b_2$) containing iso(thio)cyanate groups, contained in the component (B), are xylylenedioiso(thio)cyanate, 3,3'-dichlorodiphenyl-4,4'-diiso(thio)cyanate, 4,4'-diphenylmethanediiso(thio)cyanate, hexamethylenediiso(thio)cyanate, 2,2',5,5'-tetrachlorodiphenyl-4,4'-diiso(thio)cyanate and tolylenediiso(thio)cyanate. Further, examples of the compound ($b_2$) having at least one cyclohexyl ring are bis (iso(thio)cyanatomethyl)cyclohexane, bis(4-iso(thio)cyanatocyclohexyl)methane, bis(4-iso(thio)cyanatomethylcyclohexyl)methane, cyclohexanediiso(thio)cyanate, isophoronediiso(thio)cyanate, 2,5-bis(iso(thio)cyanatomethyl)bicyclo[2,2,2]octane, 2,5-bis(iso(thio)cyanatomethyl)bicyclo[2,2,1]heptane, 2-cyanatomethyl-3-(3-iso(thio)cyanatopropyl)-5-iso(thio)cyanatomethyl-bicyclo[2,2,1]-heptane, 2-iso(thio)cyanatomethyl-3-(3-iso(thio)cyanatopropyl)-6-iso(thio)cyanatomethylbicyclo-[2,2,]heptane, 2-iso(thio)cyanatomethyl-2-[3-iso(thio)cyanatopropyl)-5-iso(thio)cyanatomethyl-bicyclo-[2,2,1]-heptane, 2-iso(thio)cyanatomethyl-2-(3-iso(thio)cyanatopropyl)-6-(2-iso(-thio)cyanatomethyl-bicylco[2,2,1 ]-heptane, 2-iso(thio)cyanatomethyl-3-(3-iso(thio)cyanatopropyl)-6-(2-iso(-thio)cyanatoethyl)-bicyclo[2,2,1]-heptane, 2-iso(thio)cyanatomethyl-3-(3-iso(thio)cyanatopropyl)-6-(2-iso(-thio)cyanatoethyl)-bicyclo[2,2,1]-heptane, 2-iso(thio)cyanatomethyl-2-(3-iso(thio)cyanatopropyl)-5-(2-iso(-thio)cyanatoethyl)-bicyclo[2,2,1]-heptane, and 2-iso(-thio)cyanatomethyl-2-(3-iso(thio)cyanatopropyl)-6-(2-iso(thio)cyanatoethyl)-bicyclo[2,2,1]heptane.

Further, examples of the compound ($b_3$) containing vinyl and iso(thio)cyanate groups, contained in the component (B), are 2-(meth)acryloxyethyliso(thio)cyanate and (meth)acryloyliso(thio)cyanate.

When the component (B) contains vinyl group(s), it is desirable that all of the polymeric functional groups of the component (A) are mercapto groups. When the component (A) contains a hydroxy group, the polymerization degree of the polymer cannot be increased, and the resultant polymer is liable to exhibit low mechanical properties.

For the production of the optical material of this invention, monomers other than the above components (A) and (B) may be used as required.

Further, in order to improve weatherability, additives such as a UV absorber, an antioxidant, a color inhibitor, a fluorescent dye, etc., may be incorporated as required. And, a catalyst for improving polymerization reactivity may be also incorporated as required. For example, an organic peroxide, an azo compound and a basic catalyst are effective to improve the reactivity between a mercapto group and a vinyl group. An organotin compound and an amine compound are effective to improve the reactivity between a mercapto or hydroxy group and an iso(thio)cyanate group.

The following is one embodiment of the production of the optical material using the polythiol compound of this invention.

A homogeneous mixture of the above components (A) and (B), additive and catalyst is heated and cured by a known casting polymerization method, i.e. the homogeneous mixture is casted into a mold assembly formed of a combination of a pair of glass or metal molds and a resinous gasket, heated and cured. In this case, in order to make it easy to take out a molded resin, the mold may be preliminary subjected to mold releasing treatment or a mold releasing agent may be incorporated into the mixture of the components (A) and (B). The polymerization temperature differs depending upon compounds used. In general, it is between $-20°$ C. and $+150°$ C., and the polymerization time is 0.5 to 72 hours. The optical material of this invention is easily dyeable with a usual dispersion dye in water or an organic solvent, and in this case, a carrier may be added or the dye may be heated in order to ease the dyeing.

The optical material obtained as above is desirably usable as an optical product such as a plastic lens, etc., although it shall not be limited thereto.

[EXAMPLES]

This invention will be explained specifically hereinbelow by reference to Examples, which, however, shall not limit this invention.
(Evaluation of properties)

Those polythiol compounds and polymers produced therefrom which were obtained in Examples and polymers obtained in Comparative Examples were evaluated on physical properties as follows.

Refractive index ($n_D$) and Abbe's number ($\nu_D$)

Abbe's refractometer 3T supplied by Atagosha was used for the measurement.

Appearance

Observed by the eyes.

Weatherability

The hue of a plastic lens which had been set at a weatherometer provided with a sunshine carbon arc lamp for 200 hours was compared with that of a lens which remained intact. The evaluation was made on the basis of ratings of no change (o), slight yellowing (Δ) and yellowing (x).

Heat resistance

TMA measurement was carried out with a TMA apparatus supplied by Rigakusha by using a 0.5 mm$\phi$ pin under a load of 10 gf, and heat resistance was evaluated on the basis of a peak temperature of a chart obtained at a temperature elevation rate of 10° C./min.

Optical strain

Observed by the eyes according to the Schlielen method. No strain is indicated as ◯, and the presence of strain, as x.

Example 1

Preparation of 2,5-dimercaptomethyl-1,4-dithian as a polythiol compound of this invention (a compound of formula [1] in which X=H ($n_2=0$), Y=H and $n_1=1$).

25.0 Grams (0.157 mol) of bromine was added dropwise to a solution of 22.9 g (0.57 mol) of diallydisulfide in 780 ml of dichloromethane at $-78°$ C. over 1 hour. And, the temperature of the resultant mixture was elevated up to $-20°$ C., and the mixture was stirred at said temperature for 8 hours. Then, dichloromethane was removed under reduced pressure. To the remaining residue there were added 100 ml of ethanol and 23.9 g (0.314 mol) of thiourea, and the resultant mixture was refluxed for 1.5 hours. A precipitate formed was recovered by filtration, washed with ethanol several times and dried. The precipitate was dispersed in 73 ml of water, and while the resultant dispersion was refluxed under nitrogen atmosphere, 84.2 g of a 15% sodium hydroxide aqueous solution was added dropwise over 1 hour. Thereafter, the resultant mixture was further refluxed for 1 hour. The resultant reaction mixture, after cooled, was acidified with 6N-hydrochloric acid and subjected to extraction with benzene. Benzene was removed from the resultant extract under reduced pressure, and the remainder was distilled at $2\times10^{-2}$ mmHg to give 22.6 g of a fraction having a boiling point of 121.5° C. (yield 68%). This fraction had a refractive index of 1.646 and Abbe's number of 35.2. Analysis results for determining the structure of this novel polythiol compound are as follows.

| | Elemental Analysis | | |
|---|---|---|---|
| | C | H | S |
| Theoretical | 33.9 | 5.68 | 60.4 |
| Found (%) | 33.8 | 5.80 | 60.0 |

$^1$H-NMR (solvent: CDCl$_3$, internal reference substance: TMS) δ(ppm)=1.62 (t, 1H) 2.88–3.14 (m, 5H)
IR 2545 cm$^{-1}$ ($\nu_{SH}$ of thiol)

Figure 2:
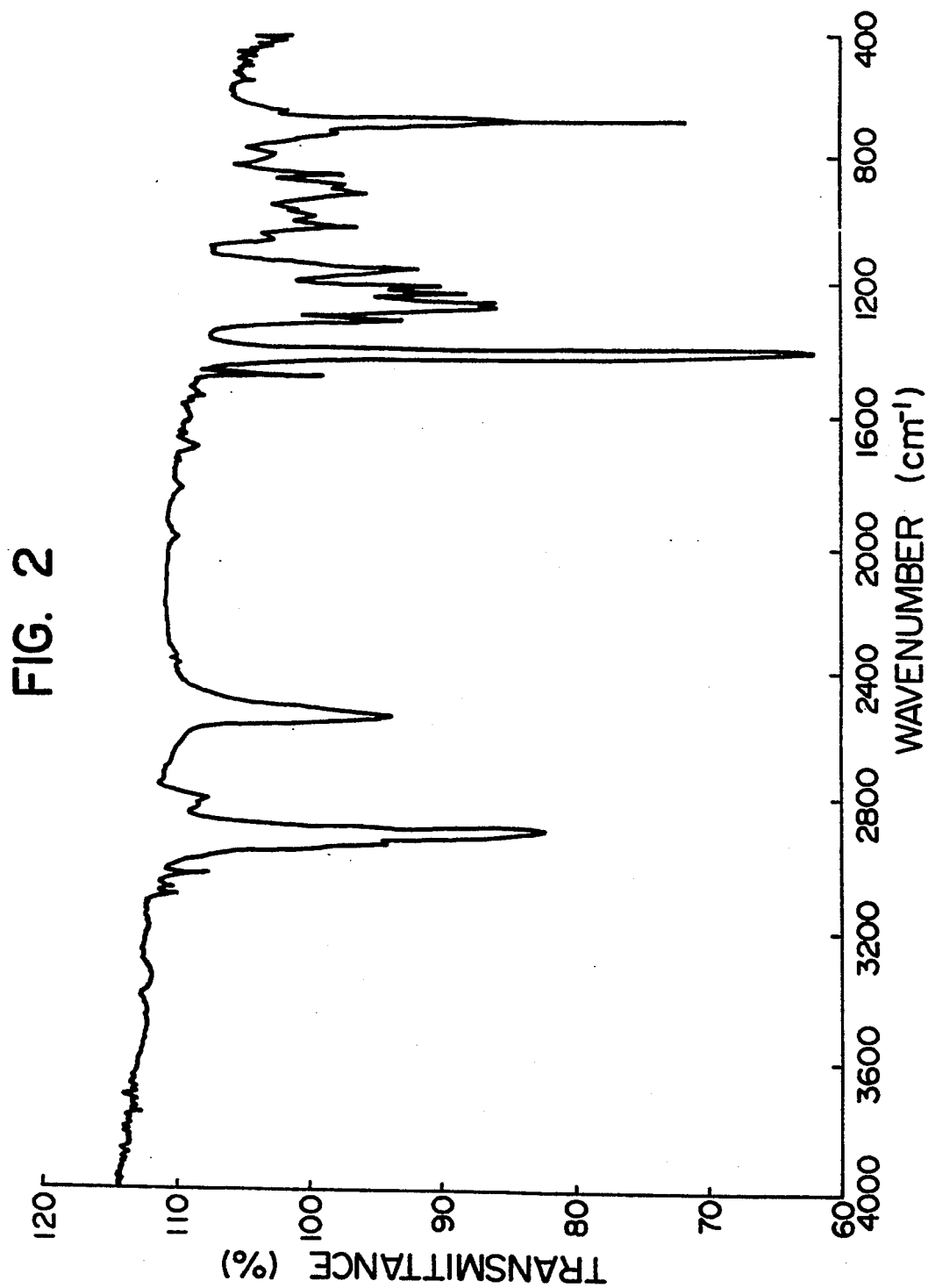

In addition, FIG. 1 shows a $^1$H-NMR spectrum chart of the above novel polythiol compound, and FIG. 2 shows an IR spectrum chart thereof.

Example 2

Preparation of 2,5-bis(2-mercaptoethylthiomethyl)-1,4-dithian as a polythiol compound of this invention (a compound of formula [1] in which X=CH$_2$CH$_2$SH ($n_2=1$), Y=H and $n_1=1$)

21.2 Grams (0.1 mol) of the 2,5-dimercaptomethyl-1,4-dithian obtained in Example 1 was dissolved in 58.7 g of a 15% sodium hydroxide aqueous solution. To the mixture was added a solution prepared by dissolving 18.0 g (0.5 mol) of thiirane in 200 ml of benzene in the presence of 100 mg of benzyltrimethylammonium chloride. And, the resultant mixture was allowed to react at room temperature for 12 hours. Then, at 0° C., while the mixture was stirred, a concentrated hydrochloric acid was added until the pH of a water phase became 1, a benzene phase was separated, the remainder was washed with water, and benzene was distilled off to give 24.6 g of an intended product, 2,5-bis(2-mercaptoethylthiomethyl)-1,4-dithian (yield 74%).

Example 3

Preparation of 2,5-bis(3-mercaptopropyl)-1,4-dithian as a polythiol compound of this invention (a compound of this invention (a compound of formula [1] in which $X=H$ ($n_2=0$), $Y=H$ and $n_1=3$)

25.0 Grams (0.157 mol) of bromine was added to a solution of 22.9 g (0.157 mol) of diallyldisulfide in 780 ml of dichloromethane at $-78°$ C. over 1 hour. And, the temperature of the mixture was elevated up to $-20°$ C., the mixture was stirred at said temperature for 8 hours, and then, dichloromethane was removed under reduced pressure. 300 Milliliters of dry tetrahydrofuran was added to the residue, the resultant mixture was cooled to $-10°$ C., and while the mixture was stirred, 329 ml of a 1.0 M-tetrahydrofuran solution of vinylmagnesium bromide was added dropwise. Thereafter, the mixture was stirred at 0° C. for 2 hours and at room temperature for 12 hours. The reaction mixture was poured into water and subjected to extraction with benzene, and benzene was distilled off under reduced pressure. Then, the resultant residue was dissolved in 200 ml of benzene, and while hydrogen sulfide was blown into the mixture, the mixture was allowed to react at room temperature for 4 hours. Thereafter, benzene was distilled off under reduced pressure to give 25.7 g of an intended product, 2,5-bis(3-mercaptopropyl)-1,4-dithian (yield 61%).

Example 4

Production of optical material of this invention

A mixture of 0.1 mol of 2,5-dimercaptomethyl-1,4-dithian (indicated as S-1 in Table 1), 0.1 mol of m-xylylenediisocyanate (indicated as XDI in Table 1) and $1\times10^{-5}$ mol of dibutyltin dilaurate (indicated as DBTDL in Table 1) was homogeneously stirred, and injected into a glass mold assembly for forming a lens. The mixture was polymerized under heat at 50° C. for 10 hours, then at 60° C. for 5 hours, and further at 120° C. for 3 hours to give a polymer having a lens form. Table 1 shows various physical properties of the polymer. As shown in Table 1, the polymer of this Example 4 was colorless and transparent, and it had a very high refractive index ($n_D$) of 1.66 and a high Abbe's number of 32 (low dispersion). Further, this polymer had excellent weatherability and heat resistance (97° C.), and it was free from optical strain.

Examples 5–25

Production of other optical materials of this invention

The procedure of Example 4 was repeated except that monomer compositions shown in Table 1 were used and that the polymerization conditions were suitably changed, whereby polymers having a lens form were obtained. Table 1 shows various physical properties of these polymers as well as those of the polymer obtained in Example 4. As shown in Table 1, the polymers of Examples 5 to 25 were also colorless and transparent, and they also had a very high refractive index ($n_D$) of 1.58 to 1.87 and a high Abbe's number of 29 to 43 (low dispersion). Further, these polymers had excellent weatherability and heat resistance (94° to 138° C.), and they were free from optical strain.

In particular, the polymers obtained in Examples 4 to 11 and 23 to 25 had an Abbe's number of 29 to 38, and these polymers had a higher refractive index, as high as 1.62 to 1.67, than conventional polymers having an Abbe's number in such a range.

Further, the polymers obtained in Examples 12 to 22 had a refractive index of 1.58 to 1.62, and these polymers had a higher Abbe's number, as high as 38 to 43, than conventional polymers having a refractive index in such a range.

Comparative Example 1

A mixture of 0.1 mol of pentaerythritoltetrakismercaptopropionate (indicated as PETMP in Table 1), 0.2 mol of m-xylylenediisocyanate (indicated as XDI in Table 1) and $1\times10^{-4}$ mol of dibutyltin dilaurate (indicated as DBTDL in Table 1) was homogeneously stirred, and injected into a glass mold assembly for forming a lens. The mixture was polymerized under heat at 50° C. for 10 hours, then at 60° C. for 5 hours, and further at 120° C. for 3 hours to give a polymer having a lens form. Table 1 shows various physical properties of the polymer. As shown in Table 1, the polymer of this Comparative Example was colorless and transparent, and exhibited no optical strain. However, this polymer had a $n_D/\nu_D$ of as low as 1.59/36, and its heat resistance was as inferior as 86° C.

Comparative Examples 2 and 3

The procedure of Comparative Example 1 was repeated except that monomer compositions shown in Table 1 were used, whereby polymers having a lens form were obtained. Table 1 shows various physical properties of these polymers as well as those of the polymers obtained in Examples 4 to 25 and those of the polymer obtained in Comparative Example 1. As shown in Table 1, the polymer of this Comparative Example 2 had a high refractive index of 1.67 and good heat resistance (94° C.). However, this polymer had inferior weatherability and exhibited optical strain. The polymer of Comparative Example 3 was colorless and transparent, and it exhibited no optical strain and had good weatherability. However, this polymer had a refractive index of as low as 1.53, and the heat resistance thereof was as inferior as 65° C.

TABLE 1

| Example No. | Component A (mol) | Component B (mol) | Polymerization catalyst (mol) | $n_D/\nu_D$ | Appearance | Heat resistance (°C.) | Weatherability | Optical strain |
| --- | --- | --- | --- | --- | --- | --- | --- | --- |
| 4 | S-1 (0.1) | XDI (0.1) | DBTDL ($1 \times 10^{-5}$) | 1.66/32 | Colorless and transparent | 97 | ◯ | ◯ |
| 5 | S-1/4-MP (0.1/0.03) | XDI (0.13) | DBTDL ($4 \times 10^{-4}$) | 1.64/34 | Colorless and transparent | 121 | ◯ | ◯ |
| 6 | S-4/PETMA/DHPS (0.1/0.04/0.01) | IPDI/TDI (0.17/0.02) | DBTDL ($1 \times 10^{-4}$) | 1.62/37 | Colorless and transparent | 98 | ◯ | ◯ |

TABLE 1-continued

| | Component A (mol) | Component B (mol) | Polymerization catalyst (mol) | $n_D/\nu_D$ | Appearance | Heat resistance (°C.) | Weather-ability | Optical strain |
|---|---|---|---|---|---|---|---|---|
| 7 | S-2/TMP/DMB (0.15/0.06/0.1) | DPMDI (0.34) | DBTDL ($2 \times 10^{-4}$) | 1.64/36 | Colorless and transparent | 101 | ○ | ○ |
| 8 | S-1/EDT (0.1/0.01) | EDMA (0.11) | ADVN ($1 \times 10^{-3}$) | 1.64/35 | Colorless and transparent | 94 | ○ | ○ |
| 9 | S-3/TMMM/1,2-BDT (0.1/0.04/0.06) | XDI/TMPTMA (0.22/0.08) | DBTDL/ADVN ($1.3 \times 10^{-4}/6 \times 10^{-3}$) | 1.67/33 | Colorless and transparent | 116 | ○ | ○ |
| 10 | S-1/PETMP (0.1/0.02) | DVB (0.14) | ADVN ($1.5 \times 10^{-3}$) | 1.63/34 | Colorless and transparent | 103 | ○ | ○ |
| 11 | S-1 (0.125) | MEI/XDI (0.1/0.1) | ADVN/DBTDL ($2 \times 10^{-3}/1 \times 10^{-5}$) | 1.62/38 | Colorless and transparent | 128 | ○ | ○ |
| 12 | S-1 (0.1) | H6-XDI (0.1) | DMTDCl ($1 \times 10^{-4}$) | 1.62/38 | Colorless and transparent | 108 | ○ | ○ |
| 13 | S-1/PETMA (0.06/0.02) | H6-XDI (0.10) | DBTDCl ($4 \times 10^{-4}$) | 1.60/40 | Colorless and transparent | 118 | ○ | ○ |
| 14 | S-2 (0.1) | H6-MDI (0.1) | DMTDCl ($2 \times 10^{-4}$) | 1.61/40 | Colorless and transparent | 98 | ○ | ○ |
| 15 | S-3 (0.06) | H6-XDI/IPDI (0.1/0.02) | DMTDCl ($2 \times 10^{-4}$) | 1.61/41 | Colorless and transparent | 135 | ○ | ○ |
| 16 | S-1/PETMP (0.08/0.01) | H6-XDI/H6-MDI (0.08/0.02) | DBTDCl ($1.5 \times 10^{-4}$) | 1.60/40 | Colorless and transparent | 121 | ○ | ○ |
| 17 | S-1/PETMP (0.35/0.075) | H6-XDI (0.5) | DMTDCl ($1 \times 10^{-4}$) | 1.60/40 | Colorless and transparent | 108 | ○ | ○ |
| 18 | S-1/1,2-DHB (0.1/0.015) | H6-XDI (0.115) | DBTDL ($3 \times 10^{-5}$) | 1.61/39 | Colorless and transparent | 100 | ○ | ○ |
| 19 | S-1/TG (0.1/0.02) | H6-XDI (0.13) | DBTDL ($3 \times 10^{-5}$) | 1.59/42 | Colorless and transparent | 109 | ○ | ○ |
| 20 | S-2/PETMA (0.06/0.02) | H6-XDI (0.1) | DMTDCl ($1 \times 10^{-5}$) | 1.60/40 | Colorless and transparent | 103 | ○ | ○ |
| 21 | S-3 (0.1) | H6-XDI (0.1) | DMTDCl ($1 \times 10^{-5}$) | 1.63/37 | Colorless and transparent | 138 | ○ | ○ |
| 22 | S-4/PETMA (0.08/0.01) | H6-XDI (0.1) | DMTDCl ($1 \times 10^{-5}$) | 1.58/43 | Colorless and transparent | 100 | ○ | ○ |
| 23 | S-2/PETMA (0.06/0.02) | XDI (0.1) | DBTDL ($1 \times 10^{-5}$) | 1.65/32 | Colorless and transparent | 101 | ○ | ○ |
| 24 | S-3 (0.1) | XDI (0.1) | DBTDL ($1 \times 10^{-5}$) | 1.67/29 | Colorless and transparent | 135 | ○ | ○ |
| 25 | S-4/PETMA (0.08/0.01) | XDI (0.1) | DBTDL ($1 \times 10^{-5}$) | 1.65/33 | Colorless and transparent | 97 | ○ | ○ |
| Comparative Example No. | | | | | | | | |
| 1 | PETMP (0.1) | XDI (0.2) | DBTDL ($1 \times 10^{-4}$) | 1.59/36 | Colorless and transparent | 86 | ○ | ○ |
| 2 | 1,3,5-TMB (0.2) | XDI (0.3) | DBTDL ($1.5 \times 10^{-4}$) | 1.67/28 | Yellowish | 94 | X | X |
| 3 | PETMP (0.1) | DAPE (0.2) | ADVN ($2 \times 10^{-3}$) | 1.53/52 | Colorless and transparent | 65 | ○ | ○ |

Abbreviations in Table 1
S-1:

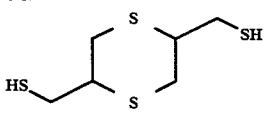

S-2:

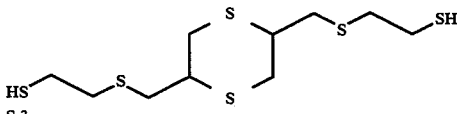

S-3:

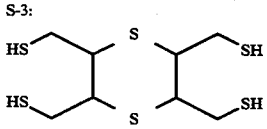

S-4:

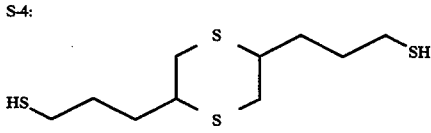

XDI: m-xylylenediisocyanate
EDT: ethanediol
PETMA: pentaerythritoltetrakismercaptoacetate EDMA: ethylene glycol dimethacrylate
PETMP: pentaerythritoltetrakismercaptopropionate
DVB: divinylbenzene 4-MP: 4-mercaptophenol
TMPTMA: trimethylolpropane methacrylate
TMP: trimethylpropane
1,2-DHB: 1,2-dihydroxybenzene
DMB: 1,3-dimercaptobenzene
TG: 3-mercapto-1,2-dihydroxypropane
DPMDI: diphenylmethanediisocyanate
TMMM: tetrakismercaptomethylmethane
1,2-BDT: 1,2-benzenedithiol
DHPS: 4,4'-dihydroxyphenylsulfide
IPDI: isophoronediioscyanate
H6-XDI: 1,3-bis(isocyanatomethyl)cyclohexane
H6-MDI: bis(4-isocyanatecyclohexyl)methane
MEI: 2-methacryloxyethylisocyanate
TDI: tolylenediisocyanate
DBTDL: dibutyltin dilaurate
DMTDCl: dimethyltin dichloride
DBTDCl: dibutyltin dichloride
ADVN: azobisdimethylvaleronitrile
1,3,5-TMB: 1,3,5-trimercaptobenzene
DAPE: diallylidenepentaerythritol The novel polythiol compound of this invention has a high refractive index and a high Abbe's number due to its 1,4-dithian ring, and it is easily polymerizable with at least one member of a compound having at least two vinyl groups per molecule, a compound having at least two iso(thio)cyanate groups per molecule and a compound having at least one vinyl group and at least one iso(thio)cyanate group per molecule to give a polymer. The optical material of this invention comprising the above polymer has a high refractive index and a high Abbe's number and also has excellent heat resistance, weatherability and transparency due to a 1,4-dithian ring contained in its main chain. Therefore, the optical material of this invention is suitably usable as a lens for spectacles, a camera, etc., a prism, an optical fiber, a recording medium substrate for use in an optical disk, a magnetic disk, etc., and an optical product such as a colored filter, a UV absorbing filter, etc.

Further, the above material is also usable in ornament utilizing its characteristic high refractive index such as a cup, a flower vase, etc.

What is claimed is:

1. A polythiol compound having the formula [1]

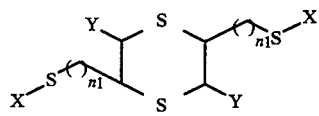

wherein X is —(CH$_2$CH$_2$S)$_{n2}$—H, Y is a hydrogen atom or —(CH$_2$)$_{n3}$—S—X, n$_1$ is an integer of 1 to 5, n$_2$ is an integer of 0 to 2, and n$_3$ is an integer of 1 to 5.

2. A polythiol compound according to claim 1, which is selected from the group consisting of the compounds represented by the formulae:

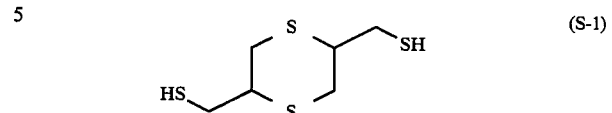 (S-1)

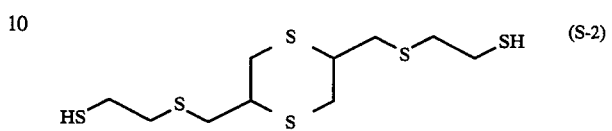 (S-2)

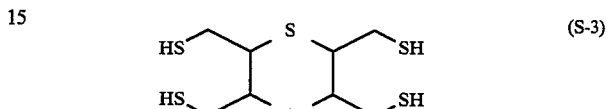 (S-3)

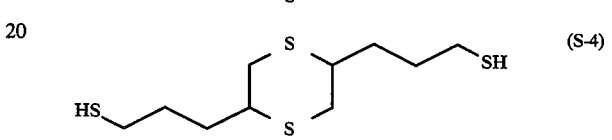 (S-4)

3. A polythiol compound having the formula

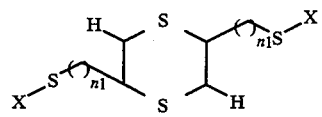

wherein X —(CH$_2$CH$_2$S)$_{n2}$—H, n$_1$ is an integer of 1 to 5, and n$_2$ is an integer of 0 to 2.

4. A polythiol compound according to claim 3, which is selected from the group consisting of the compounds represented by the formulae:

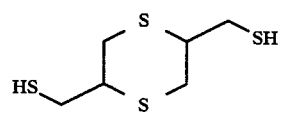

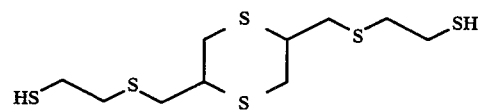

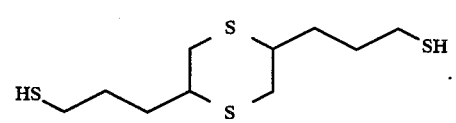

* * * * *